United States Patent [19]

Annett

[11] Patent Number: 4,886,165

[45] Date of Patent: Dec. 12, 1989

[54] HINGED CONTAINER FOR SURGICAL ARTICLES

[75] Inventor: Leland W. Annett, Lake Elmo, Minn.

[73] Assignee: Medical Concepts Development, Inc., St. Paul, Minn.

[21] Appl. No.: 307,042

[22] Filed: Feb. 7, 1989

[51] Int. Cl.⁴ .................... B65D 1/34; B65D 1/40; B65D 25/14

[52] U.S. Cl. ......................... 206/370; 206/570; 206/818; 206/350

[58] Field of Search .............. 206/370, 570, 818, 572, 206/571, 350

[56] References Cited
U.S. PATENT DOCUMENTS

| | | |
|---|---|---|
| 4,108,310 | 8/1978 | Aldridge et al. .............. 206/570 |
| 4,128,173 | 12/1978 | Lazarus et al. .............. 206/570 |
| 4,373,629 | 2/1983 | Ulin et al. .............. 206/570 |
| 4,596,329 | 6/1986 | Eldridge, Jr. .............. 206/370 |
| 4,637,513 | 1/1987 | Eldridge, Jr. .............. 206/370 |
| 4,784,267 | 11/1988 | Gessler et al. .............. 206/370 X |

*Primary Examiner*—William Price
*Attorney, Agent, or Firm*—Lawrence M. Nawrocki

[57] ABSTRACT

A disposable hinged box (2) for surgical articles. The container (2) has certain design features to facilitate accounting of small surgical implements. An oblique bifurcation between the container cover (6) and container bottom (4), together with a guard (36, 38) forms a cradle within the cover for retaining implements therein. The container is particularly suited for holding syringes within the container cover (6) and accounting for needles, or suture, within the container bottom (4).

9 Claims, 2 Drawing Sheets

HINGED CONTAINER FOR SURGICAL ARTICLES

TECHNICAL FIELD

The present invention relates to a novel hinged container for holding surgical articles. More particularly, the present invention provides a unitary hinged container with specific design features to facilitate ready accounting of the surgical articles both prior to and after a surgical procedure.

BACKGROUND OF THE INVENTION

During any surgical procedure, it is of extreme importance to maintain an exact account of the number and identity of the various medical and surgical implements employed during the procedure. That is, the exact number and identity of the implements must be noted prior to the surgical procedure so that the same number can be readily accounted for at the conclusion of the procedure.

This accounting procedure is usually performed prior to closing surgical incisions to ensure that no implements accidentally remain within the incision. Implements which are inadvertently left within an incision commonly are a source of infection and other complications. Surgical accountability is especially difficult with sponges, sutures and needles because of their extremely small size.

The hinged container of the present invention includes certain design features which render it useful in surgical accountability, especially in accounting for small surgical implements.

SUMMARY OF THE INVENTION

The container of the present invention comprises a container bottom and a container cover joined to each other along a common severable hinge. To form a closed container, the container cover is folded over the container bottom along the common hinge. The container cover engages the container bottom by a simple snap action along the common rims of the container cover and container bottom.

Of particular interest is the oblique bifurcation of the container cover and container bottom as is further described in the detailed description of the invention. Briefly, when the container is in an open position, this oblique bifurcation provides a deeper cradle portion within the cover along one side. This cradle portion is further provided with an articulated pocket or guard to organize and retain the cover contents. The oblique bifurcation of the container also provides a deeper cradle portion within the container bottom.

The floor of the container bottom is preferably provided with a magnetic pad to retain magnetic surgical articles, or with a cushioned pad to retain other small surgical articles. The floor of the container bottom, or the inserted magnetic or cushioned pad, may be further provided with indicia to facilitate surgical accountability of the articles.

The container's severable hinge allows the container cover and container bottom to be separated from each other so that they may be used as individual trays even though the entire container can initially be molded as one piece. When the surigal articles have been accounted for in the container, the container and its contents may be safely and conveniently disposed of.

DETAILED DESCRIPTION OF THE INVENTION

Figure 1:
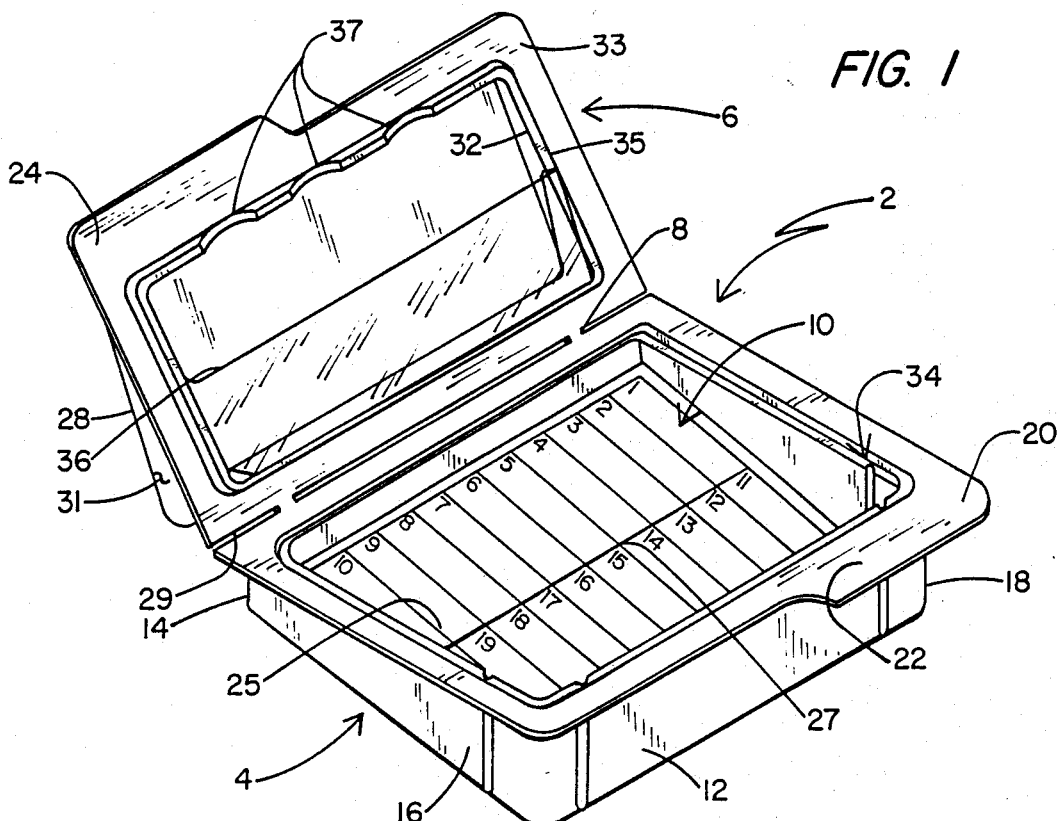
FIG. 1 is a pictorial view of an open, hinged container of the present invention showing the cover and bottom joined to each other along a severable hinge.
Figure 2:
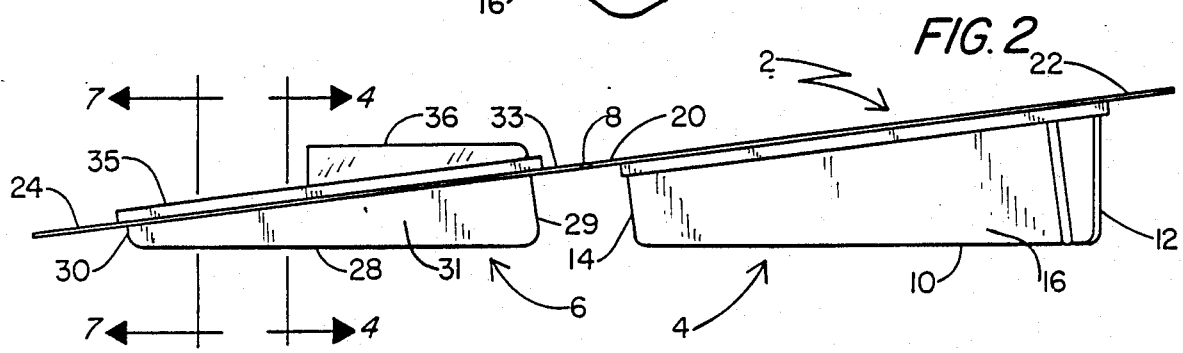
FIG. 2 is a profile view of the hinged, open container.

The hinged container 2 of this invention comprises a container bottom 4 and a container cover 6 joined to each other along a common severable hinge 8, as shown in the illustrative embodiment of this invention in FIGS. 1 and 2. Cover 6 can be separated from bottom 4 along hinge 8 so that the invention can be used as two separate trays.

Container bottom 4 has a generally rectangular floor member 10 lying generally in a first plane. Floor member 10 is preferably provided with means for accounting for surgical articles. For example, a magnetic insert 25 for retaining small metallic surgical implements, such as needles (not shown) can be employed.

Alternatively, floor member 10 may include a cushioning insert for retaining both metallic and non-metallic surgical implements, such as sponges or suture clips. The insert may also be both magnetic and cushioned.

Preferably, the chosen accounting means has a numbered grid 27 with space for individual surgical implements so that the number and identity of implements can be readily accounted for following the surgical procedure and before closing the surgical incision.

Extending upwardly from floor member 10 are four sides 12, 14, 16 and 18. The first pair of opposing sides 12 and 14 extend upwardly from floor member 10 such that side 12 is slightly taller than side 14. The second pair of opposing sides are mirror image sides 16 and 18. The four sides terminate at a generally rectangular peripheral rim 20 which extends outwardly from sides 12, 14, 16 and 18.

Figure 3:
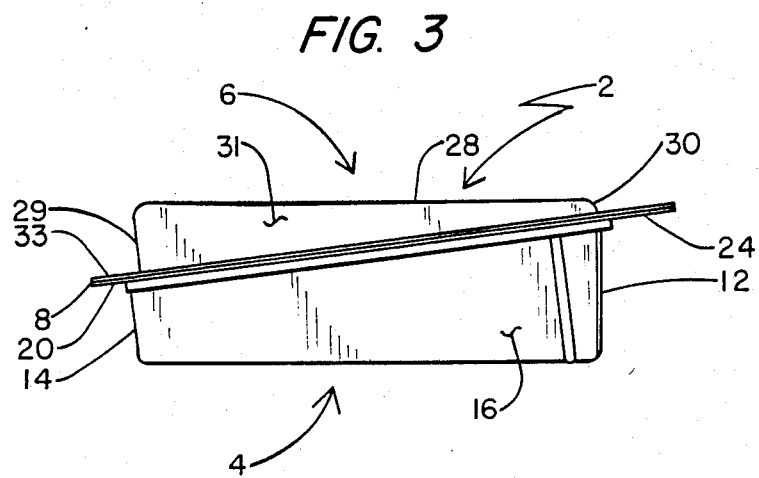
FIG. 3 is a side profile view of the hinged closed container showing the oblique bifurcation formed by the mating cover and bottom rims.
Figure 4:
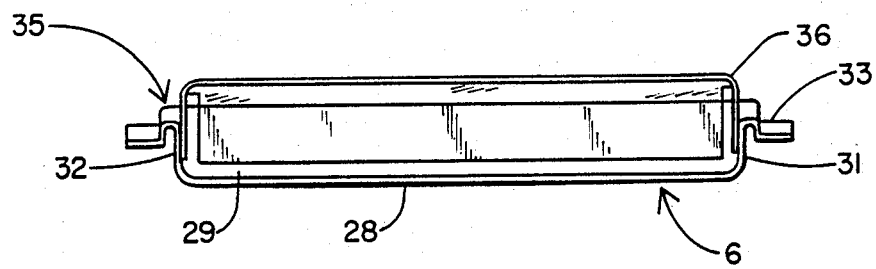
FIG. 4 is a sectional view of the container taken generally along the line 4—4 of FIG. 2.

As shown in FIGS. 1, 2 and 3, rim 20 lies generally in a second plane at an oblique angle to the first plane of floor member 10. Rim 20 along side 14 forms part of hinge 8 to container cover 6.

A female trough 34 is formed inside rim 20 and extends substantially along sides 12, 14, 16 and 18.

As shown in FIG. 1, rim 20 along side 12 forms a co-planar flange 22. Flange 22 functions as half of a thumb-and-finger opening mechanism and cooperates with a flange 24 on cover 6 as is further explained below.

FIGS. 1, 2 and 3 show container cover 6 as having generally rectangular top member 28, lying in a third plane. Extending downwardly from top member 28 are four sides 29, 30, 31 and 32. First pair of opposing sides 29 and 30 extend downwardly from top member 28 such that side 29 is slightly taller than side 30. Sides 31, 32 are opposing mirror images. Sides 20, 30, 31 and 32 terminate at a generally rectangular peripheral rim 33 which extends outwardly from sides 29, 30, 31 and 32.

Rim 33 lies generally in a fourth plane at an oblique angle to the third plane of top member 28. Rim 33 along side 29 forms part of hinge 8 to container bottom 4. A male trough 35 is provided inside rim 33 substantially surrounding sides 29, 30, 31 and 32 and aligned to cooperate with female trough 34 on container bottom 4. When cover 6 is folded over bottom 4 to form container 2, male trough 35 will cooperate with female trough 34 to retain cover 5 to bottom 4 in a snap fashion. Rim 33 along side 30 also forms a co-planar flange 24 as half of a thumb-and-finger opening mechanism to cooperate with flange 22 on the bottom 4.

As shown in FIGS. 1, 2, 4, 5 and 6, a guard 36 is attached inside of rim 33 and male trough 35 along side 29. Guard 36 forms a pocket with top member 28 and sides 31, 32.

Figure 5:
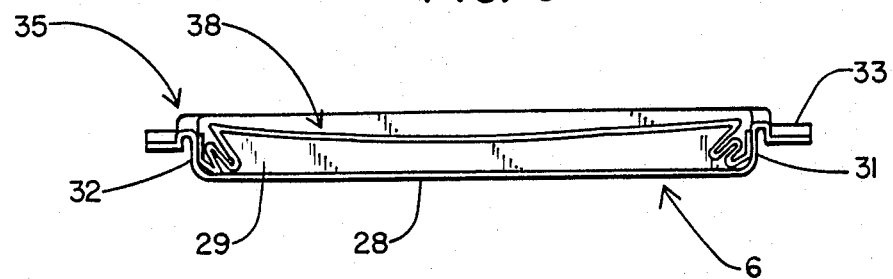
FIG. 5 is a view of the container top, similar to that of FIG. 4, showing an alternative embodiment of a guard taking the form of an articulated pocket shown in a closed configuration.
Figure 6:
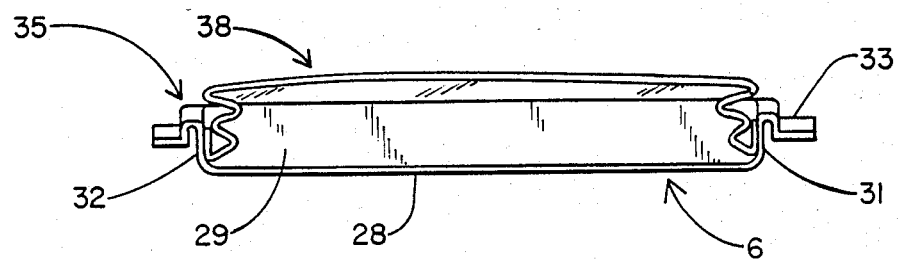
FIG. 6 is a view of the container top with the articulated pocket shown in an open configuration.
Figure 7:
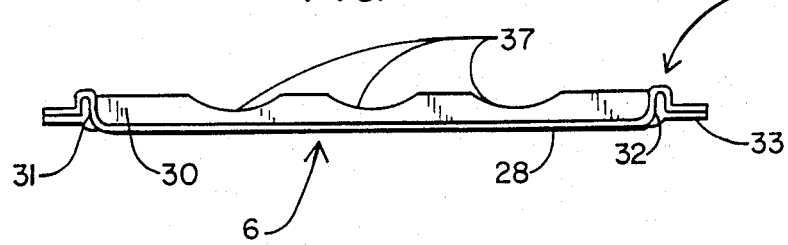
FIG. 7 is a view of the container cover, taken generally along the line 7—7 of FIG. 2, showing concave contoured rests for surgical implements such as syringes.

As shown in FIG. 5, alternative guard 38 is formed so that it will be accordian-compressed within cover 6 when container 2 is closed to provide secure retention for the contents of cover 6. As shown in FIG. 7, male trough 35 along side 30 is conveniently provided with a plurality of concave indentations 37 to ensure retention of surgical syringes or other similar elongated tubular surgical articles within cover 6 when container 2 is open.

To close container 2, cover 6 is folded over bottom 4 along hinge 8. Container 2 is formed of material which is sufficiently sturdy to allow hinge 8 to remain intact when cover 6 is folded over bottom 4, yet light enough to allow cover 6 and bottom 4 to be separated by tearing along the hinge 8. Polyvinylchloride has been found to be satisfactory, and such material also allows the container 2 to be sterilized for surgical use.

In closure, slight pressure is applied so that male trough 35 and female trough 34 engage to seal container 2. To open the closed container 2, a light thumb-and-finger opposing action is applied to flanges 22 and 24.

Numerous characteristics and advantages of the invention have been discussed. It will be understood, however, that this disclosure is only illustrative. Changes may be made in details without exceeding the scope of the invention.

What is claimed is:

1. A hinged container for surgical articles comprising:
    a container bottom and container cover joined along a common severable hinge;
    the container bottom having a generally rectangular floor member in a first plane, a first pair of opposing sides extending upwardly from the floor member such that one of said first pair of opposing sides is slightly taller than the other, a second pair of mirror image opposing sides extending upwardly from the floor member, all of the four sides terminating at a planar rim extending outwardly from the sides, the planar rim being in a second plane at an oblique angle to the first plane of the floor member, one of said first pair of opposing sides joined to the common severable hinge, a female trough inside the rim substantially surrounding the sides, and an unlatching means on the rim on the side opposite the hinge;
    the container cover including a generally rectangular top member in a third plane, a first pair of opposing sides extending downwardly from the top member such that one of said first pair of opposing sides is slightly taller than the other, a second pair of mirror image opposing sides extending downwardly from the top member, all four of the sides terminating at a planar rim extending outwardly from the sides, the planar rim of the cover being in a fourth plane at an oblique angle to the third plane of the top member, one of said first pair of opposing sides joined to the common severable hinge, a male trough inside the rim substantially surrounding the sides in cooperating alignment with the female trough on the container bottom, an unlatching means on the rim on the side opposite the hinge in cooperating alignment with the unlatching means on the container bottom, a pocket forming guard means inside the rim along the slighter taller side, forming a pocket with the top member and the mirror image sides over at least a portion of the cover; and
    accounting means located generally on the floor member for facilitating accounting of the surgical articles.

2. The means according to claim 1 wherein said accounting means further comprises indicia facilitating determination of the number of articles after a surgical procedure.

3. The container according to claim 1, wherein the portion of the male trough, opposite the pocket forming means in the container cover, is provided with concave indentations to cradle elongated surgical articles within the cover.

4. The container according to claim 3, wherein the surgical articles in the cover are syringes and the surgical articles in the bottom are needles for the syringes.

5. The container according to claim 1, wherein the pocket forming means is transparent to facilitate identification of contents.

6. The container according to claim 1 formed of polyvinylchloride.

7. The container according to claim 1, wherein the accounting means is a magnetic means for retaining metallic surgical articles.

8. The container according to claim 1, wherein the accounting means is a cushioning means.

9. The container according to claim 1, wherein the accounting means is provided with cushioning and magnetic means.

* * * * *